United States Patent
Villhauer

(10) Patent No.: US 6,617,340 B1
(45) Date of Patent: Sep. 9, 2003

(54) N-(SUBSTITUTED GLYCYL)-PYRROLIDINES, PHARMACEUTICAL COMPOSITIONS CONTAINING THEM AND THEIR USE IN INHIBITING DIPEPTIDYL PEPTIDASE-IV

(75) Inventor: Edwin Bernard Villhauer, Morristown, NJ (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/619,506

(22) Filed: Jul. 19, 2000

Related U.S. Application Data

(60) Provisional application No. 60/146,183, filed on Jul. 29, 1999.

(51) Int. Cl.⁷ .................. A61K 31/4427; C07D 401/12; C07D 403/12
(52) U.S. Cl. ................. 514/343; 546/286; 544/322; 544/335
(58) Field of Search ............................ 546/286; 514/343

(56) References Cited

U.S. PATENT DOCUMENTS

| | | | |
|---|---|---|---|
| 4,695,580 A | * | 9/1987 | Ohashi et al. |
| 5,118,811 A | | 6/1992 | Uchida et al. |
| 5,391,556 A | | 2/1995 | Heckel et al. |

FOREIGN PATENT DOCUMENTS

| | | |
|---|---|---|
| DD | 296 075 A5 | 11/1991 |
| DE | 1581 09 | 12/1982 |
| EP | 419 683 A1 | 4/1991 |
| EP | 555 824 A1 | 8/1993 |
| WO | WO 90/12005 | 10/1990 |
| WO | WO 91/16339 | 10/1991 |
| WO | WO 93/08259 | 4/1993 |
| WO | WO 95/11689 | 5/1995 |
| WO | WO 95/13069 | 5/1995 |
| WO | WO 95/15309 | 6/1995 |
| WO | WO 95/29190 | 11/1995 |
| WO | WO 95/29691 | 11/1995 |
| WO | WO 95/34538 | 12/1995 |
| WO | WO 98/19998 | 5/1998 |

OTHER PUBLICATIONS

Yamada T. et al., Bulletin of the Chemical Society of Japan, vol. 51, No. 3, pp. 878–883 (1978).
Derwent Abstract 95–302548/39 (1995).
Derwent Abstract 84–177689/29 (1984).
Derwent Abstract 96–116353 (1996).
Kaspari A. et al., Biochimica et Biophysica Acta, vol. 1293, pp. 147–153 (1996).
Ashworth D.M. et al., Bioorganic & Medicinal Chemistry Letters, vol. 6, No. 10, pp. 1163–1166 (1996).
Coutts S.J. et al., J. Med. Chem. vol. 39, pp. 2087–2094 (1996).
Deacon C.F. et al., Diabetes, vol. 44, pp. 1126–1131 (1996).
Augustyns KJL et al., European Journal of Medicinal Chemistry, vol. 32, pp. 301–309 (1997).
Hughes T.E. et al., Biochemistry, vol. 38, pp. 11597–11603 (1999).
Li J. et al., Archives of Biochemistry and Biophysics, vol. 323, No. 1, pp. 148–154 (1995).
Li J. et al., Journal of Neurochemistry, vol. 66, pp. 2105–2115 (1996).
Yamada T. et al., Bulletin of the Chemical Society of Japan, vol. 50, No. 7, pp. 1827–1830 (1977).

* cited by examiner

*Primary Examiner*—Alan L. Rotman
*Assistant Examiner*—Binta Robinson
(74) *Attorney, Agent, or Firm*—Joseph J. Borovian

(57) ABSTRACT

The invention discloses certain N-(substituted glycyl)-pyrrolidines, pharmaceutical compositions containing said compounds as an active ingredient thereof, and the use of said compounds in inhibiting dipeptidyl peptidase-IV.

18 Claims, No Drawings

US 6,617,340 B1

N-(SUBSTITUTED GLYCYL)-PYRROLIDINES, PHARMACEUTICAL COMPOSITIONS CONTAINING THEM AND THEIR USE IN INHIBITING DIPEPTIDYL PEPTIDASE-IV

This application claims the benefit of U.S. Provisional Application No. 60/146,183, filed Jul. 29, 1999.

FIELD OF THE INVENTION

The present invention relates to the area of dipeptidyl peptidase-IV inhibition and, more particularly, relates to certain N-(substituted glycyl)-pyrrolidines, pharmaceutical compositions containing said compounds, and the use of said compounds in inhibiting dipeptidyl peptidase-IV.

BACKGROUND OF THE INVENTION

Dipeptidyl peptidase-IV (DPP-IV) is a serine protease which cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium and the entry of HIV into lymphoid cells.

More recently, it was discovered that DPP-IV is responsible for inactivating glucagon-like peptide-1 (GLP-1). More particularly, DPP-IV cleaves the amino-terminal His-Ala dipeptide of GLP-1, generating a GLP-1 receptor antagonist, and thereby shortens the physiological response to GLP-1. Since the half-line for DPP-IV cleavage is much shorter than the half-life for removal of GLP-1 from circulation, a significant increase in GLP-1 bioactivity (5- to 10-fold) is anticipated from DPP-IV inhibition. Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM).

Although a number of DPP-IV inhibitors have been described in the literature, all have limitations relating to potency, stability or toxicity. Accordingly, it is clear that a great need exists for novel DPP-IV inhibitors which are useful in treating conditions mediated by DPP-IV inhibition and which do not suffer from the above-mentioned limitations of known DPP-IV inhibitors.

DESCRIPTION OF THE PRIOR ART

WO 95/15309 discloses certain peptide derivatives which are inhibitors of DPP-IV and, therefore, are useful in treating a number of DPP-IV mediated processes.

WO 95/13069 discloses certain cyclic amine compounds which are useful in stimulating the release of natural or endogenous growth hormone.

European Patent 555,824 discloses certain benzimidazolyl compounds which prolong thrombin time and inhibit thrombin and serine-related proteases.

Archives of Biochemistry and Biophysics, Vol. 323, No. 1, pgs. 148–154 (1995) discloses certain aminoacylpyrrolidine-2-nitriles which are useful as DPP-IV inhibitors.

Journal of Neurochemistry, Vol. 66, pgs. 2105–2112 (1996) discloses certain Fmoc-aminoacylpyrrolidine-2-nitriles which are useful in inhibiting prolyl oligopeptidase.

Bulletin of the Chemical Society of Japan, Vol. 50, No. 7, pgs. 1827–1830 (1977) discloses the synthesis of an aminohexapeptide, viz., Z-Val-Val-lmPro-Gly-Phe-Phe-OMe, and its related aminopeptides. In addition, the antimicrobial properties of said compounds were examined.

Bulletin of the Chemical Society of Japan, Vol. 51, No. 3, pgs. 878–883 (1978) discloses the synthesis of two known peptide antibiotics, viz., Bottromycins $B_1$ and $B_2$ according to the structures proposed by Nakamura, et al. However, since the resultant compounds were devoid of antimicrobial properties, it was concluded that the structures proposed by Nakamura, et al. were erroneous.

WO 90/12005 discloses certain amino acid compounds which inhibit prolylendopeptidase activity and, therefore, are useful in treating dementia or amnesia.

Derwent Abstract 95: 302548 discloses certain N-(aryl (alkyl)carbonyl) substituted heterocyclic compounds which are cholinesterase activators with enhanced peripheral selectivity useful in treating conditions due to the lowering of cholinesterase activity.

Chemical Abstracts 84: 177689 discloses certain 1-acyl-pyrrolidine-2-carbonitrile compounds which are useful as intermediates for proline compounds exhibiting angiotensin converting enzyme (ACE) inhibiting activity.

Chemical Abstracts 96: 116353 discloses certain 3-amino-2-mercapto-propyl-proline compounds which are Ras farnesyl-transferase inhibitors useful in treating various carcinomas or myeloid leukemias.

WO 95/34538 discloses certain pyrrolidides, phosphonates, azetidines, peptides and azaprolines which inhibit DPP-IV and, therefore, are useful in treating conditions mediated by DPP-IV inhibition.

WO 95/29190 discloses certain compounds characterized by a plurality of KPR-type repeat patterns carried by a peptide matrix enabling their multiple presentation to, and having an affinity for, the enzyme DPP-IV, which compounds exhibit the ability to inhibit the entry of HIV into cells.

WO 91/16339 discloses certain tetrapeptide boronic acids which are DPP-IV inhibitors useful in treating autoimmune diseases and conditions mediated by IL-2 suppression.

WO 93/08259 discloses certain polypeptide boronic acids which are DPP-IV inhibitors useful in treating autoimmune diseases and conditions mediated by IL-2 suppression.

WO 95/11689 discloses certain tetrapeptide boronic acids which are DPP-IV inhibitors useful in blocking the entry of HIV into cells.

East German Patent 158109 discloses certain N-protected peptidyl-hydroxamic acids and nitrobenzoyloxamides which are useful as, inter alia, DPP-IV inhibitors.

WO 95/29691 discloses, inter alia, certain dipeptide proline phosphonates which are DPP-IV inhibitors useful in the treatment of immune system disorders.

German Patent DD 296075 discloses certain amino acid amides which inhibit DPP-IV.

Biochimica et Biophysica Acta, Vol. 1293, pgs. 147–153 discloses the preparation of certain di- and tri-peptide p-nitroanilides to study the influence of side chain modifications on their DPP-IV and PEP-catalyzed hydrolysis.

Bioorganic and Medicinal Chemistry Letters, Vol. 6, No. 10, pgs. 1163–1166 (1996) discloses certain 2-cyanopyrrolidines which are inhibitors DPP-IV.

J. Med. Chem., Vol. 39, pgs. 2087–2094 (1996) discloses certain prolineboronic acid-containing dipeptides which are inhibitors of DPP-IV.

Diabetes, Vol. 44, pgs. 1126–1131 (September '96) is directed to a study which demonstrates that GLP-I amide is rapidly degraded when administered by subcutaneous or intravenous routes to diabetic and non-diabetic subjects.

SUMMARY OF THE INVENTION

The present invention provides new DPP-IV inhibitors which are effective in treating conditions mediated by DPP- IV inhibition. More particularly, the present invention relates to certain N-(substituted glycyl)-pyrrolidines which inhibit DPP-IV. In addition, the present invention provides pharmaceutical compositions useful in inhibiting DPP-IV comprising a therapeutically effective amount of a certain N-(substituted glycyl)-pyrrolidine. Moreover, the present invention provides a method of inhibiting DPP-IV comprising administering to a mammal in need of such treatment a therapeutically effective amount of a certain N-(substituted glycyl)-pyrrolidine.

DETAILED DESCRIPTION OF THE INVENTION

The essence of the instant invention is the discovery that certain N-(substituted glycyl)-pyrrolidines are useful in inhibiting DPP-IV. In one embodiment, the present invention provides compounds of formula I:

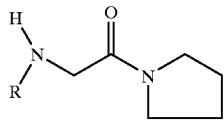

I wherein R is a group

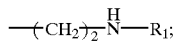

an unsubstituted ($C_{3-7}$)-cycloalkyl ring; a ($C_{3-7}$)cycloalkyl ring substituted in the 1-position by a hydroxy($C_{1-3}$)alkyl group; a group $-(CH_2)_2R_2$; a group

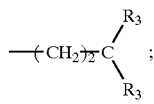

a group $-(CH_2)_3R_4$; an isopropyl group; or an isopropyl group substituted in the 1-position by a hydroxy ($C_{1-3}$)alkyl group;

$R_1$ is an unsubstituted pyridine ring; a pyridine ring mono- or di-substituted by halo, trifluoromethyl, cyano or nitro; an unsubstituted pyrimidine ring; or a pyrimidine ring monosubstituted by halo, trifluoromethyl, cyano or nitro;

$R_2$ is an unsubstituted phenyl ring; or a phenyl ring mono-, di- or tri-substituted by halo or ($C_{1-3}$)alkoxy;

each $R_3$, independently, is an unsubstituted phenyl ring; or a phenyl ring mono-substituted by halo or ($C_{1-3}$)alkoxy; and $R_4$ is a 2-oxopyrrolidine group or a ($C_{2-4}$)alkoxy group;

or a pharmaceutically acceptable acid addition salt thereof.

Preferred compounds are those of formula Ia:

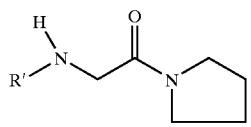

Ia where R' is a group $-(CH_2)_2N-R'_1$; an unsubstituted ($C_{3-7}$)cycloalkyl ring; a ($C_{3-7}$) cycloalkyl ring substituted in the 1-position by a hydroxy($C_{1-3}$)alkyl group; or a group $-(CH_2)_3R'_4$;

$R'_1$ is an unsubstituted pyridine ring; a pyridine ring mono- or di-substituted by halo, trifluoromethyl, cyano or nitro; or an unsubstituted pyrimidine ring; and $R'_4$ is a ($C_{2-4}$)alkoxy group;

or a pharmaceutically acceptable acid addition salt thereof.

More preferred compounds are those of formula Ib:

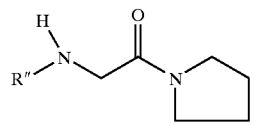

Ib where R'' is a group $-(CH_2)_2N-R''_1$; a ($C_{4-6}$)cycloalkyl ring substituted in the 1-position by a hydroxy($C_{1-3}$) alkyl group; or a group $-(CH_2)_3R'_4$;

$R''_1$ is a pyridine ring mono- or di-substituted by halo, trifluoromethyl, cyano or nitro; and $R'_4$ is as defined above;

or a pharmaceutically acceptable acid addition salt thereof.

Even more preferred compounds are those of formula Ic:

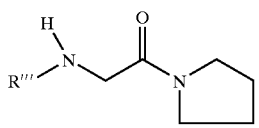

Ic where R''' is a group $-(CH_2)_2N-R'''_1$; a ($C_{4-6}$)cycloalkyl ring substituted in the 1-position by a hydroxymethyl group; or a group $-(CH_2)_3R'_4$;

$R'''_1$ is a pyridine ring monosubstituted by halo, trifluoromethyl, cyano or nitro; and $R'_4$ is as defined above;

or a pharmaceutically acceptable acid addition salt thereof.

In another embodiment, the instant invention provides pharmaceutical compositions useful in inhibiting DPP-IV comprising a pharmaceutically acceptable carrier or diluent and a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In still another embodiment, the instant invention provides a method of inhibiting DPP-IV comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In the above definitions, it should be noted that the "alkoxy" significance is either straight or branched chain, of which examples of the latter are isopropyl and t-butyl.

The acid addition salts of the compounds of formula I may be those of pharmaceutically acceptable organic or inorganic acids. Although the preferred acid addition salts are the hydrochlorides, salts of methanesulfonic, sulfuric, phosphoric, citric, lactic and acetic acid may also be utilized.

The compounds of formula I may be prepared by the following two-step reaction scheme:

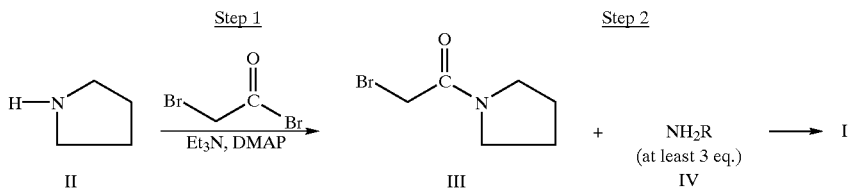

where R is as defined above.

As to the individual steps, Step 1 involves the reaction of pyrrolidine of formula II with a slight molar excess of bromoacetylbromide and triethylamine and a catalytic amount of dimethylaminopyridine (DMAP) to obtain the bromide compound of formula III. The reaction is conducted in the presence of an inert, organic solvent, preferably a chlorinated, aliphatic hydrocarbon such as methylene chloride, at a temperature of from 0° to 25° C., preferably at a temperature between 0° and 15° C., for a period of between 2 and 6 hours, preferably between 2 and 4 hours.

Step 2 concerns the reaction of the bromide compound prepared in Step 1, i.e., the bromide compound of formula III, with at least 3 equivalents of a primary amine compound of formula IV to obtain an N-(substituted glycyl)-pyrrolidine compound of formula I. The reaction is conducted in the presence of an inert, organic solvent, preferably a cyclic ether such as tetrahydrofuran, at a temperature of from 0° to 35° C., preferably at a temperature between 0° and 25° C., for a period of between 1 and 20 hours.

The primary amine compounds of formula IV are known and may be prepared by procedures well documented in the literature. For example: a) 1-hydroxymethylcyclopentylamine can be prepared by the reduction of 1-amino-1-cyclopentane carboxylic acid with lithium aluminum hydride as set forth below:

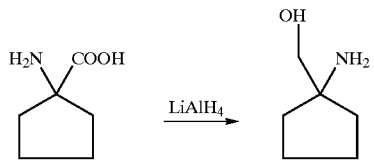

The reduction is conducted in the presence of an inert, organic solvent, preferably a cyclic ether such as tetrahydrofuran, at the reflux temperature of the solvent for a period of between 14 and 24 hours. (b) 2-[(5-chloropyridin-2-yl)amino]ethylamine can be prepared by refluxing a mixture of 2,5-dichloropyridine with ethylenediamine in an oil bath for a period of between 6 and 12 hours. (c) Similarly, 2-[(5-trifluoromethylpyridin-2-yl)amino]ethylamine can be prepared by refluxing a mixture of 2-chloro-5-trifluoromethyl pyridine with ethylenediamine in an oil bath for a period of between 6 and 12 hours. (d) 2-[(5-cyanopyridin-2-yl)amino]ethylamine can be prepared by stirring a mixture of 2-chloropyridine-5-carbonitrile and ethylenediamine at a temperature between 20° and 30° C., for a period of between 4 and 6 hours. (e) 2-[(pyrimidin-2-yl)amino]ethylamine can be prepared by adding ethylenediamine to ice-bath cooled 2-chloropyrimidine and allowing the mixture to react at a temperature between 20° and 30° C., for a period of between 12 and 20 hours.

As indicated above, the compounds of formula I form pharmaceutically acceptable acid addition salts. For example, the free base of a compound of formula I can be reacted with hydrochloric acid in gaseous form to form the corresponding mono- and di-hydrochloride salt forms, whereas reacting the free base with methanesulfonic acid forms the corresponding mesylate salt form. All pharmaceutically acceptable acid addition salt forms of the compounds of formula I are intended to be embraced by the scope of this invention.

As indicated above, all of the compounds of formula I, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of . . . intestinal cell line Caco-2" in Proc. Natl. Acad. Sci., Vol. 90, pgs. 5757–5761 (1993). Cell extract is prepared from cells solubilized in 10 mM Tris-HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 μg solubilized Caco-2 protein, diluted to a final volume of 125 μl in assay buffer (25 mM Tris-HCl pH 7.4, 140 mM NaCl, 10 mM KCl, 1% bovine serum albumin) to microtiter plate wells. The reaction is initiated by adding 25 μl of 1 mM substrate (H-Alanine-Proline-pNA; pNA is p-nitroaniline). The reaction is run at room temperature for 10 minutes after which time a 19 μl volume of 25% glacial acetic acid is added to stop the reaction. Test compounds are typically added as 30 μl additions and the assay buffer volume is reduced to 95 μl. A standard curve of free p-nitroaniline is generated using 0–500 μM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microtiter plate reader. The potency of the test compounds as DPP-IV inhibitors, expressed as $IC_{50}$, is calculated from 8-point, dose-response curves using a 4-parameter logistic function.

The following IC$_{50}$s were obtained:

| Compound | Caco-2 DPP-IV ($\mu$M) |
|---|---|
| Ex. 1 | 5.5 |
| Ex. 2A | 2.6 |
| Ex. 2B | 27.5 |
| Ex. 2C | 9.7 |
| Ex. 2D | 6.4 |
| Ex. 3 | 3.0 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, five $\mu$l of plasma are added to 96-well flat-bottom mictotiter plates (Falcon), followed by the addition of 5 $\mu$l of 80 mM MgCl$_2$ in incubation buffer (25 mM HEPES, 140 mM NaCl, 1% RIA-grade BSA, pH 7.8). After a 5 min. incubation at room temperature, the reaction is initiated by the addition of 10 $\mu$l of incubation buffer containing 0.1 mM substrate (H-Glycine-Proline-AMC; AMC is 7-amino-4-methylcoumarin). The plates are covered with aluminum foil (or kept in the dark) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 $\mu$l additions and the assay buffer volume is reduced to 13 $\mu$l. A fluorescence-concentration curve of free AMC is generated using 0–50 $\mu$M solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as IC$_{50}$, is calculated from 8-point, dose-response curves using a 4 parameter logistic function.

The following IC$_{50}$s were obtained:

| Compound | human plasma DPP-IV ($\mu$M) | rat plasma DPP-IV ($\mu$M) |
|---|---|---|
| Ex. 1 | 15.9 | 9.3 |
| Ex. 2A | 9.2 | 4.4 |
| Ex. 2B | 45.8 | 28.4 |
| Ex. 2C | 15.2 | 7.8 |
| Ex. 2D | 9.4 | 22.9 |
| Ex. 3 | 5.3 | 5.2 |

In view of their ability to inhibit DPP-IV, the compounds of formula I, and their corresponding pharmaceutically acceptable acid addition salts, are useful in treating conditions mediated by DPP-IV inhibition. For example, the compounds of formula I, and their corresponding pharmaceutically acceptable acid addition salts, improve early insulin response to an oral glucose challenge and, therefore, are useful in treating non-insulin-dependent diabetes mellitus. The ability of the compounds of formula I, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2–3 weeks were fasted for approximately 2 hours on the day of testing, divided into groups of 8–10, and dosed orally with 10 $\mu$mol/kg of the test compounds in CMC. An oral glucose bolus of 1 g/kg was administered 30 minutes after the test compound directly into the stomach of the test animals. Blood samples, obtained at various timepoints from chronic jugular vein catheters were analyzed for plasma glucose and immunoreactive insulin (IRI) concentrations, and plasma DPP-IV activity. Plasma insulin levels were assayed by a double antibody radioimmunoassay (RIA) method using a specific anti-rat insulin antibody from Linco Research (St. Louis, Mo.). The RIA has a lower limit of detection of 0.5 $\mu$U/ml with intra- and inter-assay variations of less than 5%. Data are expressed as % increase of the mean of the control animals. Upon oral administration, each of the compounds tested amplified the early insulin response which led to an improvement in glucose tolerance in the insulin resistant test animals.

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.10–100, preferably 1–75 mg/kg body weight or, for most larger primates, a daily dosage of 5–7,000, preferably 25–5,000, more preferably 50–2500 mg. A typical dosage unit is 0.5–10 mg/kg, one to three times a day.

Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The following examples show representative compounds encompassed by this invention and their synthesis. However, it should be clearly understood that they are for purposes of illustration only.

EXAMPLE 1

1-[2-[(5-chloropyridin-2-yl)amino]ethylamino] acetylpyrrolidine.

a) Preparation of 1-bromoacetylpyrrolidine.

25.0 g (350 mmol) of pyrrolidine, 39.0 g (387 mmol) of triethylamine and 200 mg of dimethylaminopyridine (DMAP) are dissolved in 200 ml of methylene chloride and the solution is then added, dropwise, to an ice-cold solution of 34.0 ml (387 mmol) of bromoacetylbromide in 200 ml of methylene chloride, over a period of 60 minutes under a calcium sulfate drying tube. The resulting clear, golden-brown solution is then stirred at ice-water temperature under a calcium sulfate drying tube, after which time, it is poured into 1.5 liters of ethyl acetate. The resulting white precipitate is filtered, washed with ethyl acetate, and the filtrate is concentrated to obtain the desired compound as a brown oil.

b) Preparation of the title compound.

To a 200 ml. flask is added 4.7 g (27 mmol) of 2-[(5-chloropyridin-2-yl)amino]ethylamine and 16 ml of tetrahydrofuran and the mixture is cooled in an ice bath. To the cooled mixture is added, dropwise, a solution of 1.74 g (91 mmol) of the compound prepared in a) above in 10 ml of tetrahydrofuran. The resultant mixture is then stirred for 1 hour at 0° C. under a calcium sulfate drying tube and then allowed to stir at room temperature for 18 hours. The solvent is then removed by rotovaping and the resultant oily paste is partitioned between methylene chloride and water. The product is then extracted into the methylene chloride layer and the aqueous layer is then washed twice with methylene chloride. The combined organic layers are then washed successively with water and brine, dried over sodium sulfate, and concentrated to obtain the desired compound in crude form. The crude form is then purified on silica gel employing a mixture of 5% methanol in methylene chloride as the eluent to yield the desired compound as an off-white solid, m.p. 118°–119° C.

EXAMPLE 2

Following essentially the procedure of Example 1b), and using in place of the amine therein, an equivalent amount of:

a) 2-[(5-cyanopyridin-2-yl)amino]ethylamine;

b) 2-[pyrimidin-2-yl)amino]ethylamine;

c) (1-hydroxymethyl)cyclopentylamine; and d) 2-[(pyridin-2-yl)amino]ethylamine;

there is obtained:

A) 1-[2-[(5-cyanopyridin-2-yl)amino]ethylamino]acetylpyrrolidine as an off-white solid, m.p., 122°–123° C.;

B) 1-[2-(pyrimidin-2-yl)amino]ethylamino]acetylpyrrolidine as a yellow wax which softens at 42° C.;

C) 1-[(1-hydroxymethylcyclopent-1-yl)amino]acetylpyrrolidine as a light yellow solid, m.p., 72°–74° C.; and D) 1-[2-[(pyridin-2-yl)amino]ethylamino]acetylpyrrolidine as a white solid, m.p., 98°–100° C., respectively.

EXAMPLE 3

1-[2-[(5-nitropyridin-2-yl)amino]ethylamino]acetylpyrrolidine dihydrochloride.

a) Preparation of the title compound in free base form.

Following essentially the procedure of Example 1b), and using in place of the amine therein, an equivalent amount of 2-[(5-nitropyridin-2-yl)amino]ethylamine, the desired compound is obtained as a golden yellow solid.

b) Preparation of the title compound.

After dissolving the free base compound prepared in a) above in 150 ml of dry tetrahydrofuran, hydrogen chloride gas is bubbled into the solution for approximately 30 seconds. The off-white precipitate that forms is then filtered, washed with dry tetrahydrofuran and the solvent is removed by high vacuum pumping to obtain the title compound as a tan solid, m.p. 220°–222° C.

What is claimed is:

1. A compound of formula I:

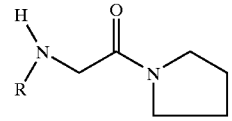

wherein R is a group —(CH$_2$)$_2$NH—R$_1$, where R$_1$ is an unsubstituted pyridine ring or a pyridine ring mono- or di-substituted by halo, trifluoromethyl, cyano or nitro;

or a pharmaceutically acceptable acid addition salt thereof.

2. A compound of formula Ib:

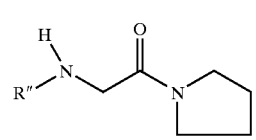

wherein R" is a group —(CH$_2$)$_2$NH—R"$_1$, where R"$_1$ is a pyridine ring mono- or a di-substituted by halo, trifluoromethyl, cyano or nitro;

or a pharmaceutically acceptable acid addition salt thereof.

3. A compound of formula Ic:

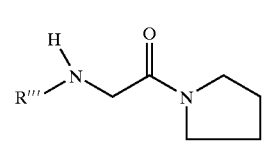

wherein R'" is a group —(CH$_2$)$_2$NH—R'"$_1$, where R'"$_1$ is a pyridine ring monosubstituted by halo, trifluoromethyl, cyano or nitro;

or a pharmaceutically acceptable acid addition salt thereof.

4. The compound according to claim 3 which is 1-[2-[(5-cyanopyridin-2-yl)amino]ethylamino]acetylpyrrolidine.

5. The compound according to claim 3 which is 1-[2-[(5-nitropyridin-2-yl)amino]ethylamino]acetylpyrrolidine, or a pharmaceutically acceptable acid addition salt thereof.

6. The compound according to claim 5 which is 1-[2-[(5-nitropyridin-2-yl)amino]ethylamino]acetylpyrrolidine dihydrochloride.

7. A pharmaceutical composition comprising a pharmaceutically acceptable carrier or diluent and a therapeutically effective amount of a compound according to claim 1, or a pharmaceutically acceptable acid addition salt thereof.

8. A pharmaceutical composition comprising a pharmaceutically acceptable carrier or diluent and a therapeutically effective amount of a compound according to claim 2, or a pharmaceutically acceptable acid addition salt thereof.

9. A pharmaceutical composition comprising a pharmaceutically acceptable carrier or diluent and a therapeutically effective amount of a compound according to claim 3, or a pharmaceutically acceptable acid addition salt thereof.

10. A pharmaceutical composition according to claim 9 comprising a therapeutically effective amount of 1-[2-[(5-cyanopyridin-2-yl)amino]ethylamino]acetylpyrrolidine.

11. A pharmaceutical composition according to claim 9 comprising a therapeutically effective amount of 1-[2-[(5-nitropyridin-2-yl)amino]ethylamino]acetylpyrrolidine, or a pharmaceutically acceptable acid addition salt thereof.

12. A pharmaceutical composition according to claim 11 comprising a therapeutically effective amount of 1-[2-[(5-nitropyridin-2-yl)amino]ethylamino]acetylpyrrolidine dihydrochloride.

13. A method of treating non-insulin-dependent diabetes mellitus comprising administering to a mammal in need of such treatment a therapeutically effective amount of a compound according to claim 1, or a pharmaceutically acceptable acid addition salt thereof.

14. A method of treating non-insulin-dependent diabetes mellitus comprising administering to a mammal in need of such treatment a therapeutically effective amount of a compound according to claim 2, or a pharmaceutically acceptable acid addition salt thereof.

15. A method of treating non-insulin-dependent diabetes mellitus comprising administering to a mammal in need of such treatment a therapeutically effective amount of a compound according to claim 3, or a pharmaceutically acceptable acid addition salt thereof.

16. A method according to claim 15 comprising administering a therapeutically effective amount of 1-[2-[(5-cyanopyridin-2-yl)amino]ethylamino]acetylpyrrolidine.

17. A method according to claim 15 comprising administering a therapeutically effective amount of 1-[2-[(5-nitropyridin-2-yl)amino]ethylamino]acetylpyrrolidine, or a pharmaceutically acceptable acid addition salt thereof.

18. A method according to claim 17 comprising administering a therapeutically effective amount of 1-[2-[(5-nitropyridin-2-yl)amino]ethylamino]acetylpyrrolidine dihydrochloride.

* * * * *

UNITED STATES PATENT AND TRADEMARK OFFICE
CERTIFICATE OF CORRECTION

PATENT NO.      : 6,617,340 B1
DATED           : September 9, 2003
INVENTOR(S)     : Edwin Bernard Villhauer It is certified that error appears in the above-identified patent and that said Letters Patent is hereby corrected as shown below:

<u>Title page,</u>
Item [*] Notice, should read as follows:
-- [*] Notice:   Subject to any disclaimer, the term of this patent is extended or adjusted under 35 U.S.C. 154(b) by 52 days. --.

Signed and Sealed this

Tenth Day of February, 2004

JON W. DUDAS
*Acting Director of the United States Patent and Trademark Office*